United States Patent [19]
Glickman et al.

[11] 3,952,066
[45] Apr. 20, 1976

[54] DERIVATIVES OF PERFLUOROALKYL IODIDE-ALLYL GLYCIDYL ETHER ADDUCTS

[75] Inventors: Samuel A. Glickman, Willingboro, N.J.; Stephen W. Osborn, Newtown, Pa.

[73] Assignee: Thiokol Corporation, Newtown, Pa.

[22] Filed: July 7, 1972

[21] Appl. No.: 269,911

[52] U.S. Cl. ............... 260/615 BF; 252/8.9; 252/36 Y; 260/348 R; 260/475 F; 260/473 R; 260/473 A; 260/484 R; 260/485 F; 260/476 R; 260/552 R; 260/609 F; 260/613 D; 260/615 F; 428/224; 428/365; 428/379; 428/390; 428/484; 428/511
[51] Int. Cl.$^2$ ............... C07C 43/00; C07C 43/01
[58] Field of Search............ 260/615 BF, 615 F

[56] References Cited
FOREIGN PATENTS OR APPLICATIONS
1,915,609 10/1970 Germany................. 260/615 F
1,233,970 6/1971 United Kingdom........... 260/615 BF

*Primary Examiner*—Howard T. Mars
*Attorney, Agent, or Firm*—Stanley A. Marcus; Royal E. Bright

[57] ABSTRACT

The derivatives of this application are based on the reaction of perfluoroalkyl iodopropyl glycidyl ethers and their dehydroiodination products, the perfluoroalkyl allyl glycidyl ethers, with active hydrogen compounds which include alcohols, carboxylic acids, water, phenols, mercaptans, mercaptoalcohols, thiourea, and hydrogen sulfide

10 Claims, No Drawings

3,952,066

DERIVATIVES OF PERFLUOROALKYL IODIDE-ALLYL GLYCIDYL ETHER ADDUCTS

BACKGROUND OF THE INVENTION

1. Field of the Invention

This invention relates to the addition of perfluoroalkyl iodides to allyl glycidyl ether to produce perfluoro compounds which contain the reactive epoxide ring which is then capable of reacting with active-hydrogen-containing-compounds. More particularly, the active hydrogen compounds include alcohols, carboxylic acids, phenols, mercaptans, mercaptoalcohols, thiourea, hydrogen sulfide and water.

These derivatives possess marked surface active properties making them suitable for use as oil and soil repellants, as stable fluids, as sealing agents, and other purposes advantageously using a mixed fluorocarbon and hydrocarbon such as plastic coating, and in textiles, rubbers, automotive waxes, furniture polishes, and personal care products.

2. Description of the Prior Art

The presently available perfluoroepoxy compounds as disclosed in U.S. Pat. No. 3,145,222 are relatively slow to react with the active hydrogen compounds thereby making the production of derivatives expensive and/or time consuming. However, by having an allyloxy, allylether, iodopropyloxy, or iodopropylether group between the perfluoro and the epoxide groups the reactivity is much greater. Additionally, the resultant corresponding derivative exhibits much improved solubility in both water and organic solvents.

Previous reactions of fluoroalkyl iodides with organic compounds have centered about the addition of polyfluoroalkyl methyl or ethyl iodides, i.e. $R_fCH_2I$ or $R_fCH_2CH_2I$, to low molecular weight aliphatic compounds to yield products wherein the iodide is on a carbon atom separated from the perfluoro group by more than one intervening carbon atoms. These previous compounds are thereby activated for dehydrohalogenation under the action of mild bases. Examples of these reactions are illustrated in the articles by Henne et al., J. Am. Chem. Soc. 73, 1791 (1951); by Haszeldine, J. Chem. Soc., London, 1199 (1953); as well as in U.S. Pat. Nos. 2,972,638; 3,016,406; and 3,408,411.

Other prior work dealt with reactions of polyfluoroalkyl iodides which would not occur by ultraviolet light initiation. Cf. U.S. Pat. No. 3,145,222. The reactions of this invention to from the basic adduct, which then is reacted to produce the derivatives herein, can proceed under ultraviolet light thereby differing from the above.

SUMMARY OF THE INVENTION

Therefore, it is an object of this invention to produce a fluorocarbon containing hydrocarbon molecule which is an active hydrogen derivative of a perfluoroalkyl iodideallyl glycidyl ether adduct.

Another object is to produce derivatives of a perfluoro-epoxide compound which have improved solubility in water and organic solvents.

Another object is to react active-hydrogen-containing-compounds with an extremely reactive epoxide group of a molecule also containing a perfluoro group.

A further object is to react alcohols, carboxylic acids, phenols, mercaptans, mercaptoalcohols, thiourea, hydrogen sulfide, and water with perfluoroalkyl allyl glycidyl ether.

A further object is to produce new compositions of matter and to advance the art.

These and other objects will become apparent in the following description and claims.

DESCRIPTION OF THE PREFERRED EMBODIMENTS

The perfluoroalkyl iodides which are suitable for use in this invention correspond to the general formulas: $C_nF_{2n+1}I$ wherein $n = 4$ to 20, preferably $n = 6$ to 16, and most preferably either 6–10, 10–16 or 10. These iodides may be prepared in any well known manner. Representative modes of preparation are illustrated in "Fluorocarbons and Their Derivatives" by R. E. Banks, London, 1964, p. 56–61; and in an article by Haszeldine, J. Chem. Soc., London, 1953, p. 3761 which are incorporated herein by reference. These perfluoroalkyl iodides are completely fluorinated and contain no hydrogen or other substituents along the alkyl chain as evidenced by the alternative representation $R_fI$. While individual iodides may be used, some advantages develop from the use of mixed alkyl groups, thereby making such a mixture suitable for use in this invention.

Allyl glycidyl ether is readily available from commercial sources.

The preparation of the perfluoroalkyl iodide-allyl glycidyl ether adduct may be carried out by a free radical reaction.

The course of the free radical reaction between a perfluoroalkyl iodide (expressed as $R_fI$) and allyl glycidyl ether is shown below. The product is a 3-perfluoroalkyl-2-iodopropyl glycidyl ether.

$$R_fI + CH_2=CH-CH_2-O-CH_2-CH\underset{O}{\overset{\diagdown\diagup}{-}}CH_2 \xrightarrow[\text{or Ultraviolet Radiation}]{\text{Free Radical Catalyst}}$$

$$R_f-CH_2-\underset{I}{CH}-CH_2-O-CH_2-CH\underset{O}{\overset{\diagdown\diagup}{-}}CH_2$$

The use of azobisisobutyronitrile catalysis at about 5 mole percent in acetone solution of 60°C. is very effective in promoting the addition of $R_fI$ to allyl glycidyl ether. An excess of the glycidyl ether is used. A heating period of 20–24 hours, under a nitrogen atmosphere may be employed to ensure complete utilization of the perfluoroalkyl iodide. The product yields are mostly in the range of 95% to quantitative.

Examples of the perfluoroalkyl iodides which may be used are a mixture of $C_6$–$C_8$–$C_{10}$ iodides of approximately 1:2:1 ratio, perfluorodecyl iodide —$C_{10}F_{21}I$, and a mixture of $C_{10}$–$C_{16}$ iodides. The presence of acidic contaminants in the perfluoroalkyl iodide may result in the polymerization of the allyl glycidyl ether.

The use of anhydrous acetone is required in these reactions to avoid water-promoted epoxide cleavage of the glycidyl ether reactant and product. The manner of product isolation via solvent distillation leads to recovery of acetone for possible re-use.

The elemental and functional analysis of the reaction products is difficult in that a mixture of homologous perfluoroalkyl iodides is employed where the exact distribution of components is not ascertainable with accuracy. Excellent agreement for percent iodine was found. The epoxy analysis was usually close to theory and usually exceeded the approximate value. Only traces of unsaturation were found, indicating nearly complete utilization of the allyl glycidyl ether. The infrared spectra of the 3-perfluorodecyl-2-iodopropyl glycidyl ether gave evidence of the presence of epoxy groups as indicated by absorption at 11.8 μ. The assignment of the 11.8 μ band to epoxy is substantiated by the literature.

Bis-(4-t-butylcyclohexyl)peroxy dicarbonate is an alternate free-radical-generating catalyst which is useful. Five mole percent of the catalyst in acetone solution at 38°–39°C. for 22 hours gives complete utilization of the perfluoroalkyl iodide. The catalyst addition may be made by an initial and an interim charge. The perfluoroalkyl iodide-allyl glycidyl ether adducts are obtained in quantitative yields. Excellent epoxy values for the products are obtained.

Ultraviolet irradiation is a highly efficient means of effecting the addition of the perfluoroalkyl iodides to allyl glycidyl ether. Irradiation may be supplied by a 140 watt Hanovia Alpine Lamp held at a distance of 2 cm. from the transparent quartz flask. A half-mole scale experiment with $C_{10}F_{21}I$ and allyl glycidyl ether in acetone at 60°C. gave a 91.8% uptake of the perfluoroalkyl iodide in 3 hours and 94.6% in 6 hours. Conversion to colorless product is in the range of 95–97%.

The removal of hydrogen iodide from the 3-perfluoroalkyl-2-iodopropyl glycidyl ethers leads to the respective perfluoroalkyl allyl ethers. Thus:

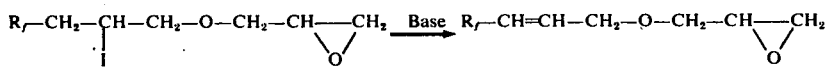

The use of excess 33% aqueous sodium hydroxide at 80°C. for a 5 hour period is an effective means of dehydroiodinating the iodine containing adducts. An excess of base is necessary. Methylene chloride may serve as an extractant for the product.

The product yield in the above procedure is usually in the vicinity of 90%. The product purity is subject to some variation. This may in part be due to epoxy ring opening as well as to the formulation of fluoroallenes.

The perfluoroalkyl iodide-allyl glycidyl ether adduct prepared as above or in any other suitable manner, or the dehydroiodinated version of the above is reacted with active-hydrogen-containing-compounds to produce the derivatives of this invention.

The reaction of substituted epoxides with active hydrogen compounds has been demonstrated in the literature to proceed via two possible routes depending upon the mode of catalysis. Thus:

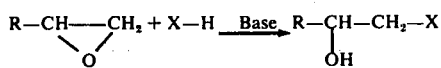

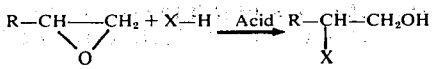

where X—H is an active hydrogen compound. It is generally recognized that basic catalysis leads to the formation of a seconday alcohol while acid catalysis leads predominately to a primary alcohol. The direction of the addition, however is not critical to the products of this invention. The fluorochemical glycidyl ethers herein are believed to react in accordance with the above generally accepted course of ring opening.

Therefore, the overall reactions of this invention may generally be expected to be as follows:

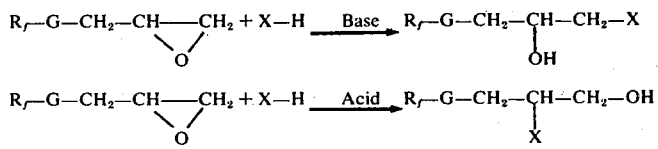

wherein
$R_f$ = the perfluoroalkyl group
G = —CH=CH—CH$_2$—O— in perfluoroalkylallyl glycidyl ethers
G = —CH$_2$—CH—CH$_2$—O— in perfluoroalkyliodo-
          |
          I
propyl glycidyl ethers
X—H = active-hydrogen-containing-compound.

When acidic catalysis is used on the iodopropyl compounds, the product is the iodopropyl product. However, when basic catalysis is used on the same iodopropyl compounds, the product is dehydroiodinated due to the reaction of the basic catalyst.

Acid catalysis has been found to be especially effective for the derivatives from hydroxyl compounds such as alcohols and phenols. Such catalysts include boron trifluoride etherate and stannic chloride. However, basic catalysts also produce a satisfactory product.

Basic catalysis has been found to be especially effective for the derivatives from carboxylic acids. A suitable catalyst includes benzyldimethylamine. Acid catalysis also works to yield a satisfactory product.

The active hydrogen containing compounds which are suitable to prepare the derivatives of this invention include alcohols, carboxylic acids, water, phenols, mercaptans, mercaptoalcohols, thiourea, and hydrogen sulfide.

Alcohols which are suitable for use in this invention include any mono- or poly-functional alcohol such as but not limited to: methyl alcohol, ethyl alcohol, propyl alcohol, isopropyl alcohol, butyl alcohol, isobutyl alcohol, hexyl alcohol, cyclohexyl alcohol, octyl alcohol, allyl alcohol, 2-methoxyethanol, 2-butoxyethanol, 2-(2-ethoxyethoxy) ethanol, 2-phenoxyethanol, ethylene glycol, glycerine, 1,3-butylene glycol, 1,4-butanediol, 1,2,4-butanetriol, butenediol, and butynediol.

Carboxylic acid which are suitable for use in this invention include any mono- or poly-functional acid such as but not limited to any of the following: acetic, propionic, butyric, formic, octanoic, lauric, stearic, oleic, succinic, glutaric, adipic, benzoic, and phthalic acids.

Suitable phenols which may be used include, but are not limited to the following: phenol, o-cresol, p-cresol, m-cresol, o-chlorophenol, p-chlorophenol, m-chlorophenol, resorcinol, hydroquinone, and hydroquinonemonomethyl ether.

Suitable mercaptans include both aliphatic and aromatic, mono- and poly-mercaptans such as, but not limited to, any of the following: butyl mercaptan, heptane mercaptan, 1-decanethiol, lauryl mercaptan, thiophenol, thiocresol, o-toluenethiol, and m-toluenethiol.

Suitable mercaptoalcohols include such as, but not limited to, the following: mercaptoethanol, mercaptopropanol, and mercaptobutanol.

The present reaction may be carried out in either a batch or continuous manner. While, for small scale preparations, the bath reaction is more convenient, the continuous reaction is more useful for commercial operations. The reaction is carried out at either atmospheric or super atmospheric pressure depending on the reactants.

The reaction temperature varies and depends primarily upon convenience. Accordingly, the temperature is generally about 70°–120°C., preferably 80°–100°C.

The reaction may be carried out in either a solvent or a non-solvent system. The only requirement for the selection of the solvent, if one is used, is that it be compatible with the catalyst. The time of reaction may vary from 1 to 30 hours or more depending upon the other conditions.

The following representative examples are given to illustrate the practice of the present invention and are not intended to limit the scope of the invention.

EXAMPLES I – VII

The reaction sequence leading to adducts of perfluoroalkyl-allyl glycidyl ethers and alcohols may be represented by the equation as follows:

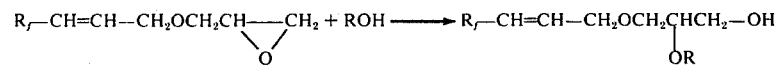

The resulting adducts may be termed 3-perfluoroalkyl-allyloxy-2-alkoxyl-1-propanols.

This reaction of the alcohol with the epoxide link of the perfluoro compound in the following cases was performed by catalysis by 0.8 mole percent boron trifluoride etherate per 1 mole of perfluoroalkyl-allyl glycidyl ether adduct at 90°C. over a 2–3 hour period. A 5 to 10% excess of the alcohol i.e., 1.05–1.10 mole/mole over the amount calculated on the epoxy equivalence of the glycidyl ether was used. The perfluoroalkyl group in each of these reactions was in the nature of a $C_6$, $C_8$, $C_{10}$ mixture of approximately a 1:2:1 ratio. The reaction alcohols are listed below. A determination by gas chromatography using a 10 foot × ¼ inch stainless steel column packed with 10% UCW 98 on Chromosorb W with a sample size of 10 microliters of a 10 weight percent solution of the product in acetone, and a temperature of elution of 80°–250°C. showed the complete utilization and lack of epoxy groups.

Vacuum stripping of the reaction products, which removed the solvent and unreactive starting materials, confirmed the utilization of the epoxy groups.

| Example | Alcohol |
|---|---|
| I | methoxy polyethyleneglycol of average molecular weight 350 |
| II | methoxy polyethyleneglycol of average molecular weight 550 |
| III | methoxy polyethyleneglycol of average molecular weight 750 |
| IV | nonylphenoxymonaoxyethylene glycol |
| V | polyethylene glycol of average molecular weight 600 |
| VI | lauryl alcohol-ethylene oxide adduct |
| VII | octadecanol |

EXAMPLES VIII – XIII

The procedure and reactions of Examples I–VII were repeated using perfluorodecyl-allylglycidyl ether in place of the mixture of alkyl groups. The results are summarized below:

| Example | Alcohol |
|---|---|
| VIII | methoxy polyethyleneglycol of average molecular weight 350 |
| IX | methoxy polyethyleneglycol of average molecular weight 550 |
| X | methoxy polyethyleneglycol of average molecular weight 750 |
| XI | nonylphenoxynonaoxyethylene glycol |
| XII | lauryl alcohol-ethylene oxide adduct |
| XIII | octadecanol |

EXAMPLES XIV – XVIII

The procedure of Examples I–VII is repeated using 3-perfluoroalkyl-2-iodopropyl glycidyl ethers instead of the dehydroiodinated glycidyl ether of the previous examples. Accordingly the reaction may be represented by:

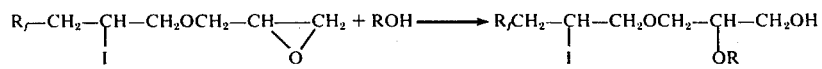

The products may be termed 3-(3'-perfluoroalkyl-2'-iodopropyloxy)-2-alkoxy-1-propanols. The alcohols listed below would enter into the above reaction. The same gas chromatography as in I–VII was used to determine the utilization of the epoxy groups.

| Example | Alcohol |
|---|---|
| XIV | methanol |
| XV | butanol |
| XVI | 2-ethylhexanol |
| XVII | cyclohexanol |
| XVIII | 2-phenylethanol |

EXAMPLES XIX – XXI

The reaction sequence leading to adducts of perfluoroalkyl-allyl glycidyl ethers and carboxylic acids may be represented by the equation as follows:

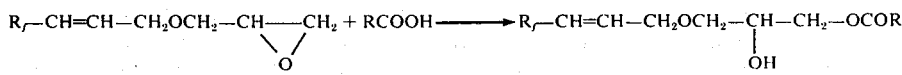

The resulting adducts may be termed 3-perfluoroalkyl-allyloxy-2-hydroxypropyl carboxylates.

These reactions of 1 mole of each material were catalyzed by benzyldimethylamine at temperatures of 95°–100°C. for 3–4 hours, at which time gas chromatographic analysis indicated 99% utilization of the epoxide. The reactions are summarized below.

| Example | $R_f$ Group | Carboxylic Acid |
|---|---|---|
| XIX | $C_{6-10}$ Mixture | Stearic Acid |
| XX | $C_{10}$ | Oleic Acid |
| XXI | $C_{10-18}$ Mixture | Dimerized Oleic Acid |

EXAMPLES XXII – XXV

The hydration reactions may be expressed as follows:

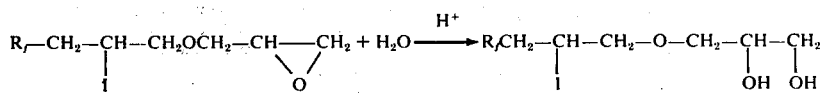

and the dehydroiodinated compound reaction is

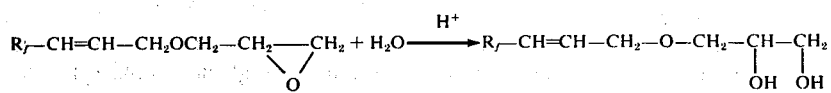

All of the reactions were conducted by heating a stirred suspension of the particular epoxide with dilute aqueous sulfuric acid at 95°C. for 9 hours.

In Examples XXII and XXIII the perfluoroalkyl substituent of the epoxide was a mixture of $C_6$, $C_8$, $C_{10}$ in approximately 1:2:1 ratio.

In Examples XXIV and XXV, the perfluoroalkyl substituent of the epoxide was perfluorodecyl.

In Examples XXII and XXIV, the iodine was present, whereas XXIII and XXV were run with the dehydroiodinated version of the perfluoroalkyl iodide-allyl glycidyl ether adducts. EXAMPLES XXVI – XXIX The reaction of a perfluoroalkyl-allyl glycidyl ether and phenols may be expressed by the following equation:

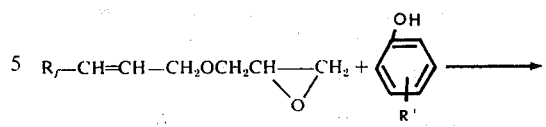

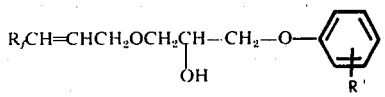

wherein R' may be hydrogen or any other substituent to yield a substituted phenol.

The resulting adducts are 3-perfluoroalkyl-allyloxy-2-hydroxy-propylphenylethers.

These reactions are catalyzed by benzyldimethylamine with equimolar amounts of the reactants being heated at 95°–100°C. for 1–8 hours, with the less acidic phenols requiring a longer reaction time. The reactions are summarized below.

| Example | $R_f$ Group | Phenolic Compound |
|---|---|---|
| XXVI | $C_{6-10}$ Mixture | Phenol |
| XXVII | $C_{10}$ | Nonyl phenol |
| XXVIII | $C_{10-16}$ Mixture | o-Cresol |
| XXIX | $C_8$ | p-Chlorophenol |

EXAMPLE XXX

A mixture of 53g (.10 mole) perfluorooctylallyl glycidyl ether, 10g (.11 mole) butyl mercaptan and .5 ml. benzyldimethylamine is heated at 85°–90°C. with stirring, in a nitrogen atmosphere for a 3 hr. period. Gas chromatographic examination would reveal the complete utilization of the glycidyl ether. The resulting mixture is then subjected to heating at 95°C. and 10 mm. to remove excess butyl mercaptan. The reaction product consists of 1-thiobutyl-3-perfluorooctylallyloxy-2-propanol in an amount of 62 grams.

EXAMPLE XXXI

The procedure of Example XXX is repeated except that 22 g. of lauryl mercaptan is employed as the mercaptan component. The reaction product consists of 1-thiolauryl-3-perfluorooctylallyloxy-2-propanol in an amount of 72 gm.

EXAMPLE XXXII

The procedure of Example XXX is repeated except that 9g. of mercaptoethanol is employed as the mercaptan component. The reaction product consists of 1-($\beta$-hydroxyethylmercapto)-3-perfluorooctylallyloxy-2-propanol in the amount of 60 gm.

EXAMPLE XXXIII

A stirred mixture of 106 g. (.20 mole) perfluorooctylallyl glycidyl ether and 1.0 ml. benzyldimethylamine is heated at 85°C. with concurrent introduction of an equimolar amount of gaseous hydrogen sulfide. Gas liquid chromatography indicates full utilization of the glycidyl ether. The reaction product comprises the addition product of hydrogen sulfide and perfluorooctylallyl glycidyl ether.

What is claimed is:

1. A compound of the formula:

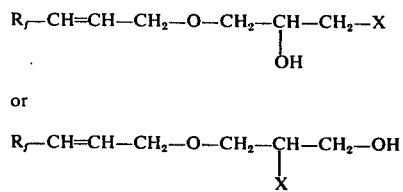

or

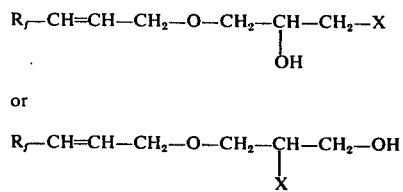

wherein $R_f$ is a perfluoroalkyl group of from 6 to 16 carbon atoms, and X is a polyetheralkoxy residue of a methoxy polyethylene glycol of average molecular weight 350 to 750 wherein said residue is the molecule minus the hydrogen of the hydroxy groups.

2. A compound as described in claim 1 wherein the methoxy polyethylene glycol is of average molecular weight 350, 550, or 750.

3. A compound according to claim 2 wherein the perfluoroalkyl residue is a mixture of $C_6$, $C_8$, $C_{10}$ in the approximate ratio 1:2:1.

4. A compound as described in claim 2 wherein the perfluoroalkyl residue in perfluorodecyl.

5. A compound as described in claim 4 wherein the methoxy polyethylene glycol is of average molecular weight 550.

6. A compound as described in claim 4 wherein the methoxy polyethylene glycol is of average molecular weight 350.

7. A compound as described in claim 4 wherein the methoxy polyethylene glycol is of average molecular weight 750.

8. A compound as described in claim 3 wherein the methoxy polyethylene glycol is of average molecular weight 350.

9. A compound as described in claim 3 wherein the methoxy polyethylene glycol is of average molecular weight 550.

10. A compound as described in claim 3 wherein the methoxy polyethylene glycol is of average molecular weight 750.

* * * * *